(12) United States Patent
Friedrichs

(10) Patent No.: US 6,926,679 B2
(45) Date of Patent: Aug. 9, 2005

(54) DEVICE AND METHOD FOR PRODUCING MEASURING DATA RELATING TO THE MOVEMENTS OF THE ABDOMINAL WALL

(75) Inventor: Arnd Friedrichs, Jena (DE)

(73) Assignee: Friendly Sensors AG, Jena (DE)

( * ) Notice: Subject to any disclaimer, the term of this patent is extended or adjusted under 35 U.S.C. 154(b) by 0 days.

(21) Appl. No.: 10/276,133

(22) PCT Filed: Apr. 19, 2001

(86) PCT No.: PCT/EP01/04441

§ 371 (c)(1),
(2), (4) Date: Jun. 12, 2003

(87) PCT Pub. No.: WO01/80737

PCT Pub. Date: Nov. 1, 2001

(65) Prior Publication Data

US 2004/0015059 A1 Jan. 22, 2004

(51) Int. Cl.[7] .............................................. A61B 5/103
(52) U.S. Cl. ....................... 600/588; 600/591; 600/304; 600/51
(58) Field of Search ................................. 600/304, 551, 600/587–593, 437, 438, 459

(56) References Cited

U.S. PATENT DOCUMENTS

| | | | | |
|---|---|---|---|---|
| 3,606,879 A | * | 9/1971 | Estes | 600/437 |
| 5,042,503 A | * | 8/1991 | Torok et al. | 600/588 |
| 5,433,201 A | * | 7/1995 | Manthey | 600/595 |
| 5,829,438 A | * | 11/1998 | Gibbs et al. | 600/588 |
| 5,935,061 A | * | 8/1999 | Acker et al. | 600/304 |
| 6,039,701 A | * | 3/2000 | Sliwa et al. | 600/588 |
| 6,171,263 B1 | * | 1/2001 | Sullivan | 600/588 |
| 6,261,247 B1 | * | 7/2001 | Ishikawa et al. | 600/587 |
| 6,270,458 B1 | * | 8/2001 | Barnea | 600/438 |

* cited by examiner

*Primary Examiner*—Robert L. Nasser
(74) *Attorney, Agent, or Firm*—Bachman & LaPointe, P.C.

(57) ABSTRACT

The invention relates to a device for producing measuring data relating to the movements of the abdominal wall of a person, comprising at least one first pair of sensor units which are configured for detachably fixing to the skin on an abdominal area of a person, a first distance apart; and a measuring device which is connected to said first pair of sensor units and which is configured for picking up signals of the sensor units that can be evaluated electrically and for producing a first distance signal corresponding to the first distance and to changes thereto. An evaluating unit is connected downstream of said measuring device. This evaluating unit is configured for evaluating pulsed and/or waved changes in the first distance signal, in such a way that non-periodical or periodical signal changes lasting at least 10 seconds, preferably more than 30 seconds, are detected, distinguished from periodical changes caused by human breathing by their frequency, amplitude or signal form, and output in the form of a display signal which can be displayed electronically or evaluated further.

13 Claims, 3 Drawing Sheets

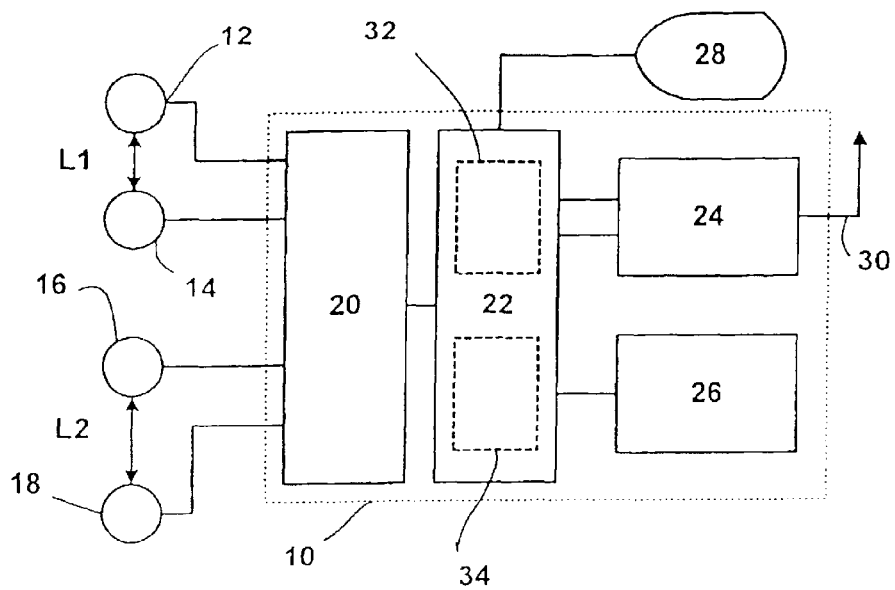
Fig. 3
Fig. 4
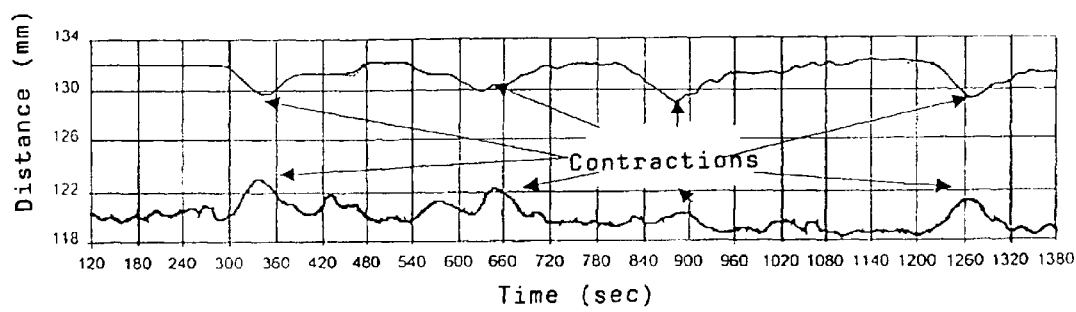
Fig. 5
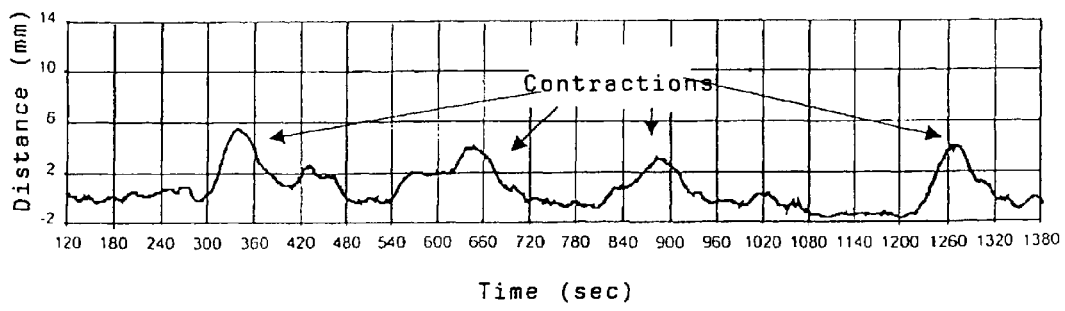

DEVICE AND METHOD FOR PRODUCING MEASURING DATA RELATING TO THE MOVEMENTS OF THE ABDOMINAL WALL

The present invention relates to a device for generating measurement data relating to movements of the abdominal wall of a person according to the introductory section of claim 1. Such a device as a general method of detecting bodily movements is known from DE 42 14 523 A1, this known device being used primarily for monitoring states and changes of the posture and locomotor system of the human being.

A very particular form of bodily movements are the contractions and dilations of the abdominal wall of a pregnant woman caused by labor pains. Known methods for measuring labor contractions are based on measurement of abdominal girth; for this purpose a strap is placed around the abdomen, the length or tension of which strap are continuously measured and recorded in writing on reel paper, for example, by means of a uterine contractions recorder.

Such known methods suffer, however, from the problem that apart from a somewhat summary measurement of abdominal girth no conclusions regarding the local progression of a labor process are possible. Although the normal case of a labor process, i.e. the change of the abdominal wall through repetitive muscular contraction of the total uterine mass, is measured with sufficient accuracy, in particular pathological labor processes and physiological transition forms are difficult to detect with known methods ("tocography") based on the stretching of a strap or change in abdominal wall tension measured by means of pressure transducers.

Whereas a normal uterine contraction generally starts in the region of the left or right tubal corner and spreads from there in a coordinated manner over the entire uterus within a period of approximately 15 seconds, different forms of contraction characterized, for example, by contractions confined to individual zones of the uterus or by uncoordinated partial contractions can occur, especially in the case of divergent excitation processes (such as imminent premature birth).

It is therefore the object of the present invention to provide an improved device for generating measurement data relating to abdominal wall movements, and in particular for detecting labor contractions, which overcomes the disadvantages of known devices for uterine contraction measurement and in particular offers the possibility of obtaining from the abdominal wall movements of a pregnant person differentiated measurement values relating to the type and character of the labor activity, with the additional purpose of detecting atypical labor activity so that a possible premature birth can be counteracted (for example by medication) in good time, thus considerably facilitating the medical care of high-risk pregnancies.

This objective presents itself against the background that, of the approximately 800 000 births per annum in Germany, approximately 6–7% occur as so-called premature births (i.e. before the tolerance range around the predetermined birth date medically assessed as normal), and it is conventionally assumed that in the case of approximately 15% of all pregnancies inhibiting-inhibiting medication therapy is indicated.

This object is met by the device with the features of claim 1 and by the method for generating measurement data with the features of claim 12; advantageous further developments of the invention are described in the subsidiary claims.

The inventive principle for capturing measurement data relating to the abdominal wall is based on measurement of a distance between the two sensor units of a pair of sensor units attached to the skin at the first (or second) distance, this distance measurement being preferably effected electronically by means of an ultrasonic or electromagnetic transmitter-receiver system as described in the generic patent DE 42 14 523, the full extent of which should be regarded as included in the present Application with regard to the electronic and constructional configuration of the distance measurement system. In particular, the principle of ultrasonic distance measurement, whereby the transit time differences in the ultrasound signal between the sensor units caused by movements of the abdominal wall are measured and evaluated, has proved advantageous for the realization of the present invention (alternatively, the use of phase differences between the transmitted and received signal is preferred).

According to the present invention this known technology is applied to the particular requirements of labor contraction measurement; in this application the distance-dependent capture of measurement data for movements of the abdominal wall, in conjunction with the evaluation unit provided according to the invention, has proved to be especially reliable and precise in allowing not merely general conclusions to be drawn regarding the presence of uterine contractions (this is effected according to the invention by means of signal-related or time-related discrimination realized by means of the evaluation unit); in particular, the provision of a plurality of pairs of sensors, according to a further development of the invention, additionally offers the possibility of precisely detecting the temporal and/or local/spatial distribution of abdominal wall movements induced by labor, and therefore of diagnosing whether said movements represent regular contractions which call for therapeutic intervention (premature inception of coordinated labor activity), or uncoordinated contractions.

Furthermore, it has emerged in the context of the invention that the actual signal form of regular uterine contractions is symmetrical with respect to the signal/time diagram; that is, the rising and falling slopes of a contraction signal measured by distance change are symmetrical with respect to a mean value. According to a further development, therefore, signal-shape detection means are provided to differentiate said signals from other signals (such as artifacts generated by sensor movement, child movements or breathing movements); these detect the presence of labor activity with high accuracy and low susceptibility to interference.

According to a preferred further development (best mode) at least two pairs of sensor units are provided, which in each case span distances which cross each other (i.e. forming approximately a right-angle). In this way the different directions of the abdominal wall movements can be measured in an especially preferred manner and, for example by summation or subtraction of the signals obtained from the two pairs of sensors, can be evaluated for still more exact measurement.

This embodiment can be further developed in that further pairs of sensors can be arranged crosswise on the abdominal wall so that the abdominal wall can be specifically observed and evaluated with respect to concrete loci of a movement (and therefore of a contraction of the underlying uterus).

Furthermore, it is especially preferred to detect, in addition to the signal captured and transmitted according to the invention, a breathing signal of the person monitored, this being accomplished in the context of the invention likewise by evaluation of the signal obtained by the length-dependent distance measurement according to the invention: breathing, too, gives rise (with the breathing frequency of approx. 0.2

Hz) to periodic movements of the abdominal wall, these signals being, however, reliably discriminated from the distance signals characteristic of labor contractions in the context of the invention. The additionally active monitoring of the breathing signal therefore makes it possible not only to improve the quality of the labor contraction signal itself but also reliably to detect critical conditions, such as the absence of breathing signals (sleep-apnoea states, hyperventilation states) and to take appropriate countermeasures.

The present invention is especially suitable for use with a portable unit, and more preferably with a portable unit co-operating by means of wireless data exchange with a base station. In this way the present invention makes it possible to locate the units provided for measurement data capture and evaluation according to the invention, which are conventionally realized by means of suitably programmed controllers, in a portable battery-operated housing which can be carried about continuously by the pregnant person and which makes possible permanent monitoring of labor activity around the clock, including the establishment of a labor profile which allows observation of the intervals between contractions, etc.

In particular in view of the, in some cases, very onerous nature of the antenatal period for the pregnant person, therefore, the present invention not only allows reliable monitoring of labor activity without stationary connection to a known uterine contraction recording device, but also enhances the pregnant person's feeling of security, while providing a considerable increase in convenience.

To sum up, with the present invention an instrument and a method are created which are not only suited to distinguishing critical from normal labor conditions quickly and reliably (and thereby enabling assistance to be quickly provided and superfluous administering of medication avoided); in addition, through the portable realization of the invention, an extremely advantageous instrument for increasing flexibility and convenience in pregnancy monitoring is provided.

Further advantages, features and details of the invention will be apparent from the following description of preferred embodiments and with reference to the drawings, in which:

FIG. 3 shows an alternative embodiment with two pairs of sensor units to the outputs of which a portable measurement and transmission device is connected;

FIG. 4 is a signal/time diagram for the two sensor pairs shown in FIG. 3 as individual signals;

FIG. 5 shows a difference signal formed from the individual signals of FIG. 4;

Figure 1:
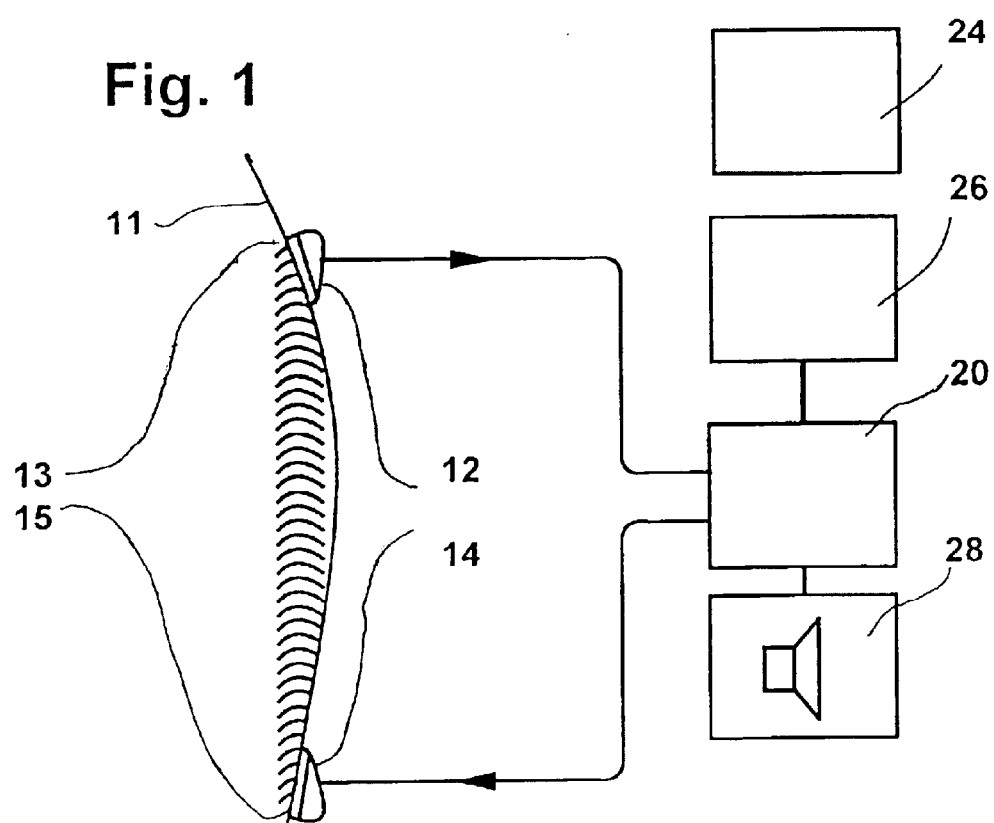
FIG. 1 is a schematic view of the device according to the invention for generating measurement data at a position on the abdominal wall with a single pair of sensor units to the outputs of which functional units are connected.

FIG. 1 shows schematically how a first sensor unit 12 and a second sensor unit 14 are attached at a predetermined distance apart L1 (FIG. 3) on an abdominal wall 11 of a pregnant person, at respective sensor positions 13 and 15.

The sensor units 12, 14 are associated with the transmitters and receivers of an ultrasonic distance measuring unit 20 which, on the basis of transit time differences accompanying changes of the distance L1 between the sensor units 12, 14 (or the positions 13, 15), outputs in otherwise known manner a corresponding signal suitable for further evaluation.

In terms of hardware, as shown schematically in FIG. 1, an evaluation and output unit 28 is connected to an output of the distance measurement unit 20 and deduces the characteristic presence of a contraction as a reaction to the distance measurement signal from the unit 20, in particular from the fact that a change in the distance signal of a predetermined minimum amplitude is present over an interval of typically more than 30 seconds, usually in the range between 1 and 1.5 minutes, and accordingly outputs a contraction signal. Parallel thereto, a contraction signal is stored in an evaluation and memory unit 26, in particular in order to monitor intervals between successive contractions, and the labor monitor, shown in FIG. 1 and realized in the simplest manner, is connected wirelessly by means of a communication unit 24 (shown only schematically) to a base station for further monitoring and evaluation of the signal.

Figure 2:
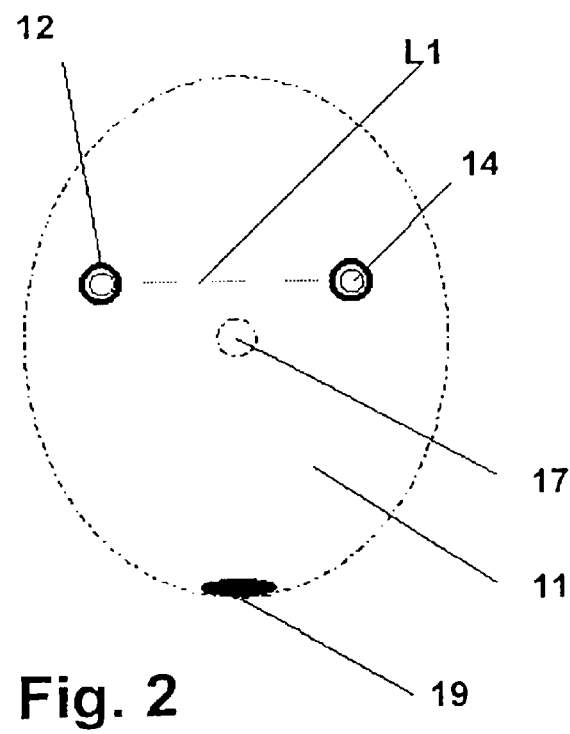
FIG. 2 is a schematic view from above of the abdominal wall showing the position of the sensor units.

With regard to this—simplest—application (i.e. with only one pair of sensor units), FIG. 2 clarifies how a length L1 is formed the between the individual sensors 12, 14, which length changes as a function of the dependent-dependent abdominal wall movement of the pregnant person and can be evaluated in the context of the present invention. In FIG. 2 reference numeral 17 symbolically designates the navel, and reference numeral 19 the symphysis.

Figure 6:
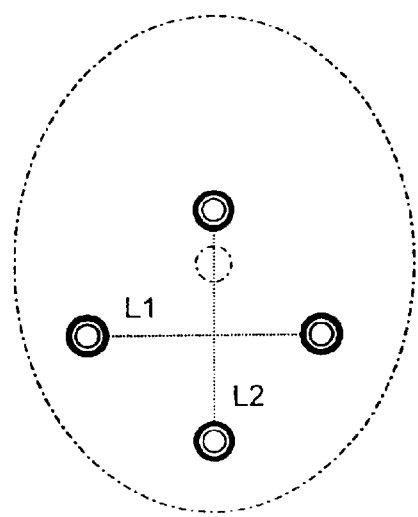
FIGS. 6, 7 show a clarifying representation of the displacement of the positions and distances of the respective pairs of sensors as a reaction to a contraction.

With reference to FIG. 3 a further embodiment of the present invention is described; in this embodiment the first pair of sensor units 12, 14 is supplemented by a second pair of sensor units 16, 18, which are spaced apart by a further distance L2 and the units of which are so arranged on the abdominal wall 11, for example, in the manner shown in FIG. 6, that the imaginary lines L1, L2 cross between the respective pairs of sensor units.

As shown in FIG. 3, the ultrasonic distance measurement unit 20 receives the distance signals of both pairs of sensor units, and therefore two individual signals which are shown in exemplary fashion as a signal/time diagram in FIG. 4. The upper curve, shown with a thin line, represents the signal pattern between the second pair of sensors 16, 18, and therefore the change of the distance L2, while the lower signal curve, drawn with a thick line, corresponds to the distance L1 between the first pair of sensors 12, 14. Characteristic labor activity is indicated by the arrows, whereby it emerges that a typical contraction signal on both channels (12/14, 16/18) is at least 30, typically 60 to 90 seconds long, has a substantially symmetrical curve shape in the time diagram and occurs at intervals which are markedly longer than the contraction signal itself.

An evaluation unit 22, connected to the output of the measurement unit 20 in FIG. 3, is provided for processing and analysis of the more complex (as compared to FIG. 1) signal pattern and, in the above-described manner, transmits a signal to the output unit 28 as a reaction to a detected labor activity. The communication unit 24 (realized with the symbolic antenna 30 as a radio unit or a suitably configured mobile telephone unit), and the memory unit 26, are activated for storage of the signal pattern detected and for observation and analysis of successive contraction signals.

As shown in FIG. 5, not only is the evaluation unit 22 shown in FIG. 3 able to observe and evaluate the two measurement channels 12/14 and 16/18 discretely with regard to labor activity, but also a difference signal is formed from these two signals and shows characteristic contractions in a far clearer manner, as shown in FIG. 5. By means of this signal processing measure, therefore, the resolution and accuracy in the recognition of contractions, or of abdominal wall movements characteristic of contractions, can be further enhanced.

FIG. 3 additionally clarifies by means of functional units 32, 34 that a detailed analysis of the received signal curves with respect to contraction-specific signal patterns can be effected (unit 12), while monitoring of the measured distance signal with respect to breathing signals (unit 34) is additionally possible. These latter signals occur typically at a frequency of approx. 0.2 Hz and can likewise be recognized as characteristic movements (and, of course, as short movements in comparison to contractions) of the abdominal wall, with the signal form according to FIGS. 4 and 5.

The embodiment shown in FIG. 3 therefore makes it possible to carry out in an especially favorable manner monitoring of the breathing activity of the pregnant person in addition to the monitoring of labor, whereby not only is the actual quality of recognition of labor processes enhanced but, in addition, breathing can be monitored for critical states, and the degree of safety achieved by the device according to the invention is therefore considerably increased.

Figure 7:
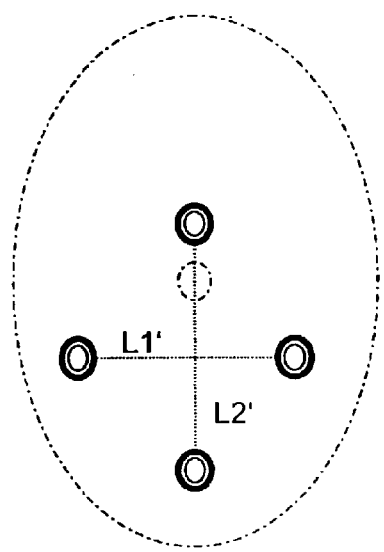

According to further developments the present invention is suited to capturing distance and movement signals of a multiplicity of pairs of sensors. Thus, although the configuration shown in FIGS. 6 and 7 represents an especially appropriate, two-channel evaluation (for example, as in FIGS. 3 to 5), FIG. 7 showing the typical length change L1', L2' of the monitored distances L1, L2 in case of labor activity (the abdominal wall is represented symbolically in a somewhat stretched condition), in principle any further desired arrangements including additional pairs of sensors are possible.

Figure 8:
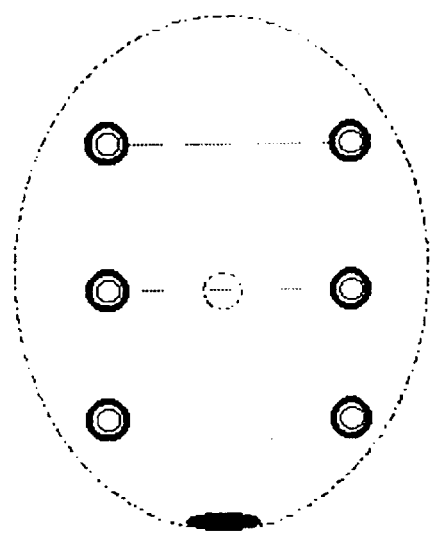
FIGS. 8, 9 show exemplary configurations of the arrangement of a plurality of sensor pairs for detecting a local distribution of movement or labor activity on the abdominal wall.
Figure 9:
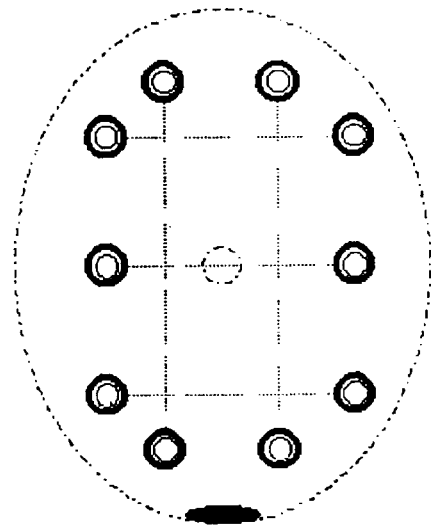

Typical examples are shown in FIGS. 8 and 9, in which the pairs of sensors and the lines extending between them cover practically completely the area of the abdominal wall relevant to uterine contraction measurement, and therefore can not only detect in a particularly appropriate manner movement activity in different areas of the abdominal wall but also provide the basis for a time-dependent evaluation of these location-related data; in other words, they provide the precondition for distinguishing, for example, contractions which take place exclusively in one partial area of the abdominal wall and are therefore manifested in a clearly delimited movement, from movement patterns which begin in a partial area and then extend over the entire abdominal wall and are observable as successive signals of adjacent sensor units in a time progression.

In this way the present invention makes it possible in a manner not conceivable up to now not only to recognize contractions as such but to detect potentially pathological or critical labor conditions and to distinguish said conditions reliably from abdominal movements corresponding to regular labor processes. Accordingly, an evaluation unit connected to the output of configurations as shown in FIGS. 8, 9 is provided with a corresponding number of evaluation channels, and the evaluation electronics, conventionally realized by means of digital technology (programmed controller units), are able to distinguish these temporal and/or spatial patterns appropriately and to correlate them with different specific movement patterns.

According to another further development, not shown in the drawings, a preferably automated dispensing or dosing unit is connected to the output of the evaluation unit, which dispensing or dosing unit automatically initiates the administering of a corresponding medication or substance to the pregnant person as a reaction to an evaluation of the contraction signal, in particular to a critical reduction in the intervals between individual contractions. This can be effected, for example, by means of otherwise known dosing pumps which, in the present application, are filled with, for example, contraction-inhibiting medications or an analgesic and dispense a predetermined dose of medication, for example intravenously, as soon as a pre-adjustable, critical time interval between successive contractions (concretely, between characteristic changes in the movement signal recognized as contractions) is exceeded.

To sum up, the present invention not only permits labor activity to be reliably monitored and quantified, but also enables labor contractions to be distinguished from other values (breathing activity, child movement, artifacts); according to further developments these other values can be used for additional evaluation, and in its practical realization as a portable output unit (reference numeral 10 in FIG. 3) the present invention imparts to the pregnant person an extremely high degree of convenience at the same time as maximized monitoring security.

What is claimed is:

1. A device for generating measurement data relating to movements of the abdominal wall of a person, comprising:
at least one first pair of sensor units which are configured for detachable fixing to the skin on an abdominal area of a person, spaced apart by a first distance (L1),
a measuring device connected to the first pair of sensor units and configured for detecting signals of the sensor units which can be electronically evaluated, and for generating a first distance signal corresponding to the first distance (L1) and changes thereto;
an evaluation unit connected to an output of the measuring device, where the evaluation unit evaluates pulsed and/or waveform changes in the first distance signal by:
(1) identifying non-periodic or periodic changes lasting at least 10 seconds;
(2) distinguishing the changes lasting at least 10 seconds from periodic changes caused by human breathing by identifying whether the signal has a form that is symmetrical with respect to a signal/time diagram of the first distance signal, and
(3) outputting an output signal which can be displayed or evaluated further.

2. A device according to claim 1, including at least one second pair of sensor units configured for detachable fixing to the skin on the abdominal area of the person and spaced apart by a second distance (L2), a first line corresponding to the first distance (L1) and connecting the first pair of sensor units being arranged at a predetermined angle to a second line corresponding to the second distance and connecting the second pair of sensor units.

3. A device according to claim 2, wherein the predetermined angle is greater than 0°.

4. A device according to claim 2, wherein the predetermined angle is a right-angle.

5. A device according to claim 2, wherein the first and second pairs of sensor units are provided to be so attachable that the first line and the second line cross on the abdominal area (11).

6. A device according to claim 2, wherein the evaluation unit is configured for summation or subtraction of the first distance signal with respect to a second distance signal output by the second pair of sensor units.

7. A device according to claim 2, including means for detecting a spatial and temporal expansion of a movement of the abdominal wall from an evaluation of the first distance signal and at least one second distance signal output by the at least one second pair of sensor units.

8. A device according to claim 1, wherein the evaluation unit is configured for additional generation of a breathing display signal which is generated as a reaction to changes of the first distance signal determined by human breathing detected according to frequency, amplitude and/or signal form.

9. A device according to claim 1, including analysis and storage means associated with the evaluation unit and configured for electronic storage of the display signal and for detecting a time interval between successive display signals.

10. A device according to claim 9, including an alarm unit associated with the analysis and storage means which is configured for comparing the detected time interval with a predetermined, preset time value and for outputting an alarm signal if a predefined number of successive detected time intervals falls below the preset time value.

11. A device according to claim 1, wherein the measuring device and the evaluation unit are components of a portable, battery-operated unit which is connectable, by means of a wireless data connection, for transmission of the display signal and/or further signals to a stationary base unit.

12. A device according to claim 1, wherein the evaluation unit is additionally configured for detection of a characteristic change in the first and/or second distance signal caused by a foetal child movement in the abdomen of the person and manifested by a characteristic movement of the abdominal wall.

13. A device according to claim 1, including means for the automated dispensing of a medication, for intravenous introduction of the medication into a vessel of the person, the introduction means being connected to the evaluation unit and being so configured that administering of a medication can be triggered as a reaction to the case when successive signal changes fall below a predetermined, preset time interval.

* * * * *